United States Patent [19]

Lucas

[11] Patent Number: 5,579,399
[45] Date of Patent: Nov. 26, 1996

[54] ACOUSTIC RESONATOR HAVING MODE-ALIGNMENT-CANCELLED HARMONICS

[75] Inventor: Timothy S. Lucas, Richmond, Va.

[73] Assignee: Macrosonix Corporation, Richmond, Va.

[21] Appl. No.: 279,156

[22] Filed: Jul. 22, 1994

Related U.S. Application Data

[60] Continuation of Ser. No. 226,469, Apr. 12, 1994, abandoned, which is a division of Ser. No. 881,339, May 11, 1992, Pat. No. 5,319,938.

[51] Int. Cl.$^6$ ................................................ H04R 25/00
[52] U.S. Cl. ............................ 381/165; 381/192; 62/6
[58] Field of Search ........................... 381/192, 194, 381/199, 201, 165, 166, 162, 59; 62/6, 647

[56] References Cited

U.S. PATENT DOCUMENTS

| | | | |
|---|---|---|---|
| 3,772,466 | 11/1973 | Hossbach | 381/192 |
| 4,114,380 | 9/1978 | Ceperley | 62/467 |
| 4,355,517 | 10/1982 | Ceperley | 62/467 |
| 4,398,398 | 8/1983 | Wheatley et al. | 62/467 |
| 4,607,382 | 8/1986 | Dijkstra et al. | 381/59 |
| 4,722,201 | 2/1988 | Hofler et al. | 62/467 |
| 4,858,441 | 8/1989 | Wheatley et al. | 62/467 |
| 4,953,366 | 9/1990 | Swift et al. | 62/467 |
| 5,165,243 | 11/1992 | Bennett | 62/6 |
| 5,231,336 | 7/1993 | van Namen | 318/128 |
| 5,231,337 | 7/1993 | van Namen | 318/128 |

OTHER PUBLICATIONS

Blackstock "Finite–Amplitude Motion of a Piston in a Shallow, Fluid–Filled Cavity", The Journal of the Acoustical Society of America, vol. 34, No. 6, Jun. 1962, pp. 796–802.

D. Felipe Gaitan et al., "Finite Amplitude Standing Waves in Harmonic and Anharmonic Tubes", J. Acoust. Soc. Am., May 5, 1993, pp. 2489–2495.

Alan B. Coppens et al., "Finite–Amplitude Standing Waves Within Real Cavities", J. Acoust. Soc. Am., vol. 58, No. 6, Dec. 1975, pp. 1133–1140.

Institute of Vibration Research At The Technical University of Berlin, "A Method for the Production of Extremely Powerful Standing Sound Waves in Air", Hermann Oberst. (1940) (Translation from German).

Stephen Weiner, "Standing Sound Waves of Finite Amplitude", J. Acoust. Soc. Am., vol. 40, No. 1 (1966), pp. 241–243.

Abbott A. Putnam, *Combustion–Driven Oscillations in Industry*, American Elsevier Publishing Co., 1971, pp. 156–208.

P. Merkli & H. Thomann, "Transistion to Turbulance in Oscillating Pipe Flow", J. Fluid Mech., 1975, vol. 68, Part 3, pp. 567–576.

Samuel Temkin, "Propagating and Standing Sawtooth Waves", J. Acoust. Soc. Am., vol. 45, No. 1, pp. 224–227.

Donald B. Cruikshank, Jr., "Experimental Investigation of Finite–Amplitude Acoustic Oscillations in a Closed Tube", J. Acoust. Soc. Am., vol. 52, No. 3 (Part 2), pp. 1024–1036.

*Primary Examiner*—Curtis Kuntz
*Assistant Examiner*—Huyen D. Le
*Attorney, Agent, or Firm*—Foley & Lardner

[57] ABSTRACT

An acoustic resonator includes a chamber which contains a fluid. The chamber has a geometry which produces self-destructive interference of at least one harmonic in the fluid to avoid shock wave formation at finite acoustic pressure amplitudes. The chamber can have reflective terminations at each end or a reflective termination at only one end. A driver mechanically oscillates the chamber at a frequency of a selected resonant mode of the chamber. The driver may be a moving piston coupled to an open end of the chamber, an electromagnetic shaker or an electromagnetic driver.

8 Claims, 9 Drawing Sheets

| MEASURED DATA FOR THE RESONATOR OF FIG. 3 | | | |
|---|---|---|---|
| NUMBER | HARMONICS (Hz) | RESONATOR MODES (Hz) | $f_n - nf_1$ (Hz) |
| 1 | 333.94 | 333.94 | 0 |
| 2 | 667.88 | 541.36 | -126.52 |
| 3 | 1001.82 | 811.45 | -190.37 |
| 4 | 1335.76 | 1145.22 | -190.54 |
| 5 | 1669.70 | 1427.07 | -242.63 |
| | | | Ideal Shift = 166.97 |

| THEORETICAL DATA FOR THE RESONATOR OF FIG. 3 | | | |
|---|---|---|---|
| NUMBER | HARMONICS (Hz) | RESONATOR MODES (Hz) | $f_n - nf_1$ (Hz) |
| 1 | 333.17 | 333.17 | 0 |
| 2 | 666.35 | 543.56 | -122.79 |
| 3 | 999.52 | 811.56 | -187.97 |
| 4 | 1332.70 | 1148.42 | -184.27 |
| 5 | 1665.87 | 1435.33 | -230.54 |
| 6 | 1999.04 | 1659.01 | -340.03 |
| 7 | 2332.22 | 1951.01 | -381.20 |
| 8 | 2665.39 | 2261.64 | -403.75 |
| 9 | 2998.57 | 2537.50 | -461.07 |
| 10 | 3331.74 | 2784.92 | -546.83 |
| | | | Ideal Shift = 166.58 |

FIG. 7

| MEASURED DATA FOR THE RESONATOR OF FIG. 6 ||||
| --- | --- | --- | --- |
| NUMBER | HARMONICS (Hz) | RESONATOR MODES (Hz) | $f_n - nf_1$ (Hz) |
| 1 | 317.60 | 317.60 | 0 |
| 2 | 635.20 | 462.80 | -142.40 |
| 3 | 952.80 | 801.20 | -151.60 |
| 4 | 1270.04 | 1105.30 | -165.10 |
| 5 | 1588.00 | 1330.60 | -257.40 |
| 6 | 1905.60 | 1612.20 | -293.40 |
| 7 | 2223.20 | 1877.50 | -345.70 |
|  |  |  | Ideal Shift = 158.80 |

FIG. 8

| THEORETICAL DATA FOR THE RESONATOR OF FIG. 6 ||||
| --- | --- | --- | --- |
| NUMBER | HARMONICS (Hz) | RESONATOR MODES (Hz) | $f_n - nf_1$ (Hz) |
| 1 | 317.62 | 317.62 | 0 |
| 2 | 635.23 | 497.66 | -137.57 |
| 3 | 952.85 | 801.98 | -150.87 |
| 4 | 1270.47 | 1123.65 | -146.82 |
| 5 | 1588.08 | 1351.35 | -236.74 |
| 6 | 1905.70 | 1637.36 | -268.34 |
| 7 | 2223.32 | 1926.85 | -296.46 |
| 8 | 2540.93 | 2205.06 | -335.88 |
| 9 | 2858.55 | 2467.33 | -391.22 |
| 10 | 3176.17 | 2734.50 | -441.66 |
|  |  |  | Ideal Shift = 158.80 |

FIG. 10

| THEORETICAL DATA FOR THE RESONATOR OF FIG. 9 | | | |
|---|---|---|---|
| NUMBER | HARMONICS (Hz) | RESONATOR MODES (Hz) | $f_n - nf_1$ (Hz) |
| 1 | 296.19 | 296.19 | 0 |
| 2 | 592.38 | 469.87 | -122.51 |
| 3 | 888.57 | 793.77 | -94.80 |
| 4 | 1184.76 | 1043.87 | -140.88 |
| 5 | 1480.95 | 1358.57 | -122.37 |
| 6 | 1777.13 | 1643.16 | -133.97 |
| 7 | 2073.32 | 1922.00 | -151.32 |
| 8 | 2369.51 | 2208.06 | -161.45 |
| 9 | 2665.70 | 2489.70 | -176.00 |
| 10 | 2961.89 | 2776.13 | -185.76 |
| 11 | 3258.08 | 3051.98 | -206.10 |
| 12 | 3554.27 | 3329.33 | -224.94 |
| 13 | 3850.46 | 3588.04 | -262.41 |
| 14 | 4146.65 | 3865.40 | -281.25 |
| 15 | 4442.84 | 4125.49 | -317.35 |
| | | | Ideal Shift = 148.09 |

ACOUSTIC RESONATOR HAVING MODE-ALIGNMENT-CANCELLED HARMONICS

BENEFIT OF EARLIER FILING IN THE UNITED STATES

This application is a continuing application of U.S. application Ser. No. 08/226,469 filed Apr. 12, 1994, now abandoned, which is a division of U.S. application Ser. No. 07/881,339 filed May 11, 1992, now U.S. Pat. No. 5,319,938, issued Jun. 14, 1994.

REFERENCE TO RELATED APPLICATIONS

This application is related to my copending U.S. application Ser. No. 07/665,316 filed Mar. 6, 1991 and my copending U.S. application Ser. No. 07/493,580 filed Mar. 14, 1990.

BACKGROUND OF THE INVENTION

1) Field of Invention

This invention relates to an acoustic resonator in which near-linear macrosonic waves are generated in a resonant acoustic chamber, having specific applications to resonant acoustic compressors.

2) Description of Related Art

My earlier U.S. Pat. No. 5,020,977 is directed to a compressor for a compression evaporation cooling system which employs acoustics for compression. The compressor is formed by a standing wave compressor including a chamber for holding a fluid refrigerant. A travelling wave is established in the fluid refrigerant in the chamber. This travelling wave is converted into a standing wave in the fluid refrigerant in the chamber so that the fluid refrigerant is compressed.

Heretofore, the field of linear acoustics was limited primarily to the domain of small acoustic pressure amplitudes. When acoustic pressure amplitudes become large, compared to the average fluid pressure, nonlinearities result. Under these conditions a pure sine wave will normally evolve into a shock wave.

Shock evolution is attributed to a spacial change in sound speed caused by the large variations in pressure, referred to as pressure steepening. During propagation the thermodynamic state of the pressure peak of a finite wave is quite different than its pressure minimum, resulting in different sound speeds along the extent of the wave. Consequently, the pressure peaks of the wave can overtake the pressure minimums and a shock wave evolves.

Shock formation can occur for waves propagating in free space, in wave guides, and in acoustic resonators. The following publications focus on shock formation within various types of acoustic resonators.

Temkin developed a method for calculating the pressure amplitude limit in piston-driven cylindrical resonators, due to shock formation (Samuel Temkin, "Propagating and standing sawtooth waves", J. Acoust. Soc. Am. 45, 224 (1969)). First he assumes the presence of left and right traveling shock waves in a resonator, and then finds the increase in entropy caused by the two shock waves. This entropy loss is substituted into an energy balance equation which is solved for limiting pressure amplitude as a function of driver displacement. Temkin's theory provided close agreement with experimentation for both traveling and standing waves of finite amplitude.

Cruikshank provided a comparison of theory and experiment for finite amplitude acoustic oscillations in piston-driven cylindrical resonators (D. B. Cruikshank "Experimental investigation of finite-amplitude acoustic oscillations in a closed tube", J. Acoust. Soc. Am. 52, 1024 (1972)). Cruikshank demonstrated close agreement between experimental and theoretically generated shock waveforms.

Like much of the literature, the work of Temkin and Cruikshank both assume piston-driven cylindrical resonators of constant cross-sectional (CCS) area, with the termination of the tube being parallel to the piston face. CCS resonators will have harmonic modes which are coincident in frequency with the wave's harmonics, thus shock evolution is unrestricted. Although not stated in their papers, Temkin and Cruikshank's implicit assumption of a sawtooth shock wave in their solutions is justified only for CCS resonators.

For resonators with non-harmonic modes, the simple assumption of a sawtooth shock wave will no longer apply. This was shown by Weiner who also developed a method for approximating the limiting pressure amplitude in resonators, due to shock formation (Stephen Weiner, "Standing sound waves of finite amplitude", J. Acoust. Soc. Am. 40, 240 (1966)). Weiner begins by assuming the presence of a shock wave and then calculates the work done on the fundamental by the harmonics. This work is substituted into an energy balance equation which is solved for limiting pressure amplitude as a function of driver displacement.

Weiner then goes on to show that attenuation of the even harmonics will result in a higher pressure amplitude limit for the fundamental. As an example of a resonator that causes even harmonic attenuation, he refers to a T shaped chamber called a "T burner" used for solid-propellent combustion research. The T burner acts as a thermally driven ½ wave length resonator with a vent at its center. Each even mode will have a pressure antinode at the vent, and thus experiences attenuation in the form of radiated energy through the vent. Weiner offers no suggestions, other than attenuation, for eliminating harmonics. Attenuation is the dissipation of energy, and thus is undesirable for energy efficiency.

Further examples of harmonic attenuation schemes can be found in the literature of gas-combustion heating. (see for example, Abbott A. Putnam, *Combustion-Driven Oscillations in Industry* (American Elsevier Publishing Co., 1971)). Other examples can be found in the general field of noise control where attenuation-type schemes are also employed, since energy losses are of no importance. One notably different approach is the work of Oberst, who sought to generate intense sound for calibrating microphones (Hermann Oberst, "A method for the production of extremely powerful standing sound waves in air", Akust. Z. 5.27 (1940)). Oberst found that the harmonic content of a finite amplitude wave was reduced by a resonator which had non-harmonic resonant modes. His resonator was formed by connecting two tubes of different diameter, with the smaller tube being terminated and the larger tube remaining open. The open end of the resonator was driven by an air jet which was modulated by a rotating aperture disk.

With this arrangement, Oberst was able to produce resonant pressure amplitudes up to 0.10 bar for a driving pressure amplitude of 0.02 bar, giving a gain of 5 to the fundamental. The driving waveform, which had a 30% error (i.e. deviation from a sinusoid), was transformed to a waveform of only 5% error by the resonator. However, he predicted that if more acoustic power were applied, then nonlinear distortions would become clearly evident. In fact, harmonic content is visually noticeable in Oberst's waveforms corresponding to resonant pressure amplitudes of only 0.005 bar.

Oberst attributed the behavior of these finite amplitude waves, to the non-coincidence of the resonator modes and the wave harmonics. Yet, no explanations were offered as to the exact interaction between the resonator and the wave harmonics. Oberst's position seems to be that the reduced spectral density of the resonant wave is simply the result of comparatively little Q-amplification being imparted to the driving waveform harmonics. This explanation is only believable for the modest pressure amplitudes obtained by Oberst. Oberst provided no teachings or suggestions that his methods could produce linear pressure amplitudes above those which he achieved, and he offered no hope for further optimization. To the contrary,, Oberst stated that nonlinearities would dominate at higher pressure amplitudes.

A further source of nonlinearity in acoustic resonators is the boundary layer turbulence which can occur at high acoustic velocities. Merkli and Thomann showed experimentally that at finite pressure amplitudes, there is a critical point at which the oscillating laminar flow will become turbulent (P. Merkli, H. Thomann, "Transition to turbulence in oscillating pipe flow", J. Fluid Mech., 68, 567 (1975)). Their studies were also carried out in CCS resonators.

Taken as a whole, the literature of finite resonant acoustics seems to predict that the inherent nonlinearites of fluids will ultimately dominate any resonant system, independent of the boundary conditions imposed by a resonator. The literature's prediction of these limits is far below the actual performance of the present invention.

Therefore, there is a need in the art to efficiently generate very large shock-free acoustic pressure amplitudes as a means of gas compression for vapor-compression heat transfer systems of the type disclosed in my U.S. Pat. No. 5,020,977. Further, many other applications wig the field of acoustics, such as thermoacoustic heat engines, can also benefit from the generation of high amplitude sinusoidal waveforms.

SUMMARY OF THE INVENTION

It is an object of the present invention to provide acoustic resonators which eliminate shock formation by promoting the destructive self-interference of the harmonics of a wave, whereby near-linear acoustic pressures of extremely high amplitude can be achieved.

It is another object of the present invention to provide acoustic resonators which minimize the nonlinear energy dissipation caused by the boundary layer turbulence of finite acoustic waves.

It is a further object of the present invention to provide acoustic resonators which minimize boundary viscous energy dissipation and boundary thermal energy dissipation.

It is a still further object of the present invention to provide an acoustic driving arrangement for achieving high acoustic pressure amplitudes.

It is an even further object of the present invention to provide an acoustic resonator which can maintain near-sinusoidal pressure oscillations while being driven by harmonic-rich waveforms.

The acoustic resonator of the present invention includes a chamber containing a fluid. The chamber has a geometry which produces destructive self interference of at least one harmonic in the fluid to avoid shock wave formation at finite acoustic pressure amplitudes. The chamber has a cross-sectional area which changes along the chamber, and the changing cross-sectional area is positioned along the chamber to reduce an acoustic velocity of the fluid and/or to reduce boundary viscous energy dissipation. The chamber may comprise a resonant chamber for a standing wave compressor used for fluid compression for heat transfer operations.

The acoustic resonator driving system of the invention includes a chamber containing a fluid, wherein the chamber has acoustically reflective terminations at each end. A driver mechanically oscillates the chamber at a frequency of a selected resonant mode of the chamber. The acoustic resonator and drive system of the present invention may be connected to heat exchange apparatus so as to form a heat exchange system such as a vapor-compression system.

As described above, the acoustic resonator and acoustic driving arrangement of the present invention provide a number of advantages and achieve non-linear acoustic pressures of extremely high amplitude. In particular, the actual performance of the present invention is far beyond the results predicted in the literature of finite resonant acoustics.

These and other objects and advantages of the invention will become apparent from the accompanying specifications and drawings, wherein like reference numerals refer to like parts throughout.

BRIEF DESCRIPTION OF THE DRAWINGS

FIG. 7 is a table of measured data for the resonator shown in FIG. 6;

FIG. 8 is a table of theoretical data for the resonator shown in FIG. 6;

FIG. 10 is a table of theoretical data for the resonator shown in FIG. 9;

DETAILED DESCRIPTION OF THE PREFERRED EMBODIMENTS

Shock Elimination via Mode-Alignment-Canceled Harmonics

It is well known that "pressure steepening" at high acoustic pressure amplitudes leads to the classic sawtooth waveform of a shock wave. It is also understood that a sawtooth waveform implies, from Fourier analysis, the presence of harmonics.

If finite amplitude acoustic waves are generated in a constant cross-sectional (CCS) resonator, a shock wave will appear having the harmonic amplitudes predicted by the Fourier analysis of a sawtooth waveform. At first this would not seem surprising, but it must be understood that a CCS resonator has modes which are harmonic (i.e. integer multiples of the fundamental) and which are coincident in frequency with the harmonics of the fundamental. CCS resonators can be considered as a special case of a more general class of resonators whose modes are non-harmonic. Non-harmonic resonators hold a previously unharnessed potential for providing extremely high amplitude linear waves. This potential is realized by non-harmonic resonators which are designed to promote the self-destructive interference of the harmonics of the fundamental.

The present invention employs this principle and provides a new resonator design criterion; to optimize the self-cancellation of wave harmonics. This new design criterion for mode-alignment-canceled harmonics (MACH) eliminates shock formation. MACH resonators have achieved pressure amplitudes of 100 psi peak-to-peak, with mean pressures of 80 psia, without shock formation. This translates into a peak acoustic pressure amplitude which is 62% of the mean pressure.

Once the MACH design criterion is understood, many different resonator geometries can be employed for aligning a resonator's higher modes to promote self-cancellation of harmonics. A straightforward approach for exploiting the MACH principle is to align resonator modes to fall between their corresponding harmonics.

Figure 1:
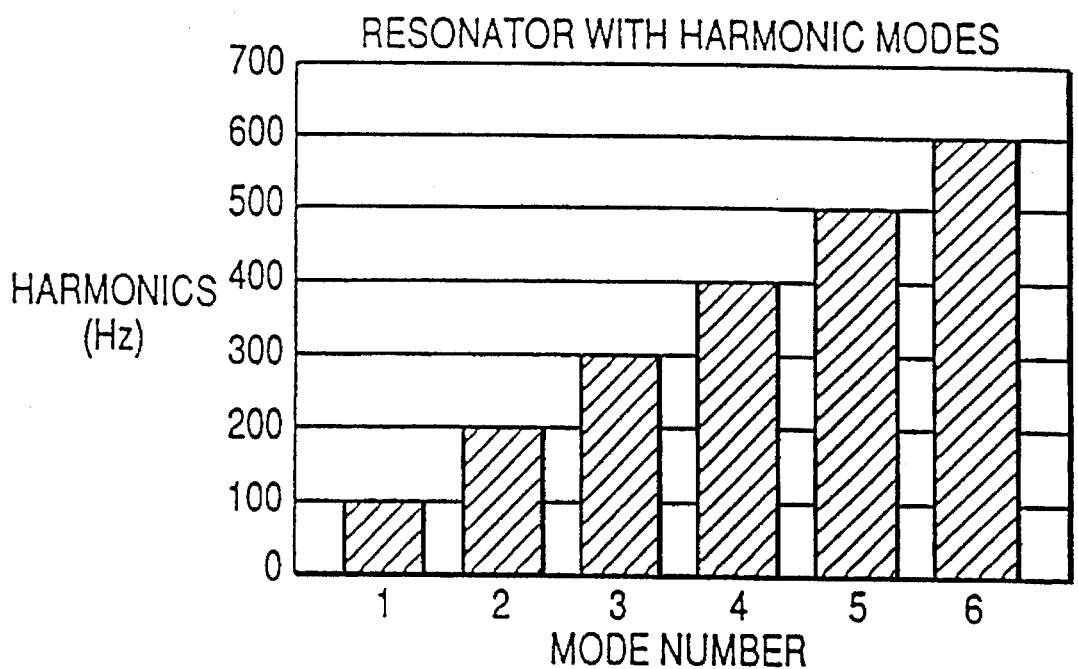
FIG. 1 is a graphical representation of a resonator having higher modes which are harmonics (i.e. integer multiples) of the fundamental.

The bar graph of FIG. 1 illustrates the relationship between the harmonics of the fundamental and the resonator modes for a CCS ½ wave length resonator. The vertical axis marks the wave harmonics of the wave, and the bar height gives the resonant frequency of the mode. At a fundamental frequency of 100 Hz the wave will have harmonics at 200 Hz, 300 Hz, 400 Hz, etc. From FIG. 1 it can be seen that the harmonics of the wave are coincident in frequency with the modes of the resonator. Stated differently, the nth harmonic of the wave is coincident with the nth mode of the resonator. Consequently, little or no self-destructive interference of the wave harmonics will occur, and a shock wave can evolve without restriction. For a well developed shock wave, the pressure amplitude of the 2nd harmonic will be within 6 dB of the fundamental's amplitude.

Figure 2:
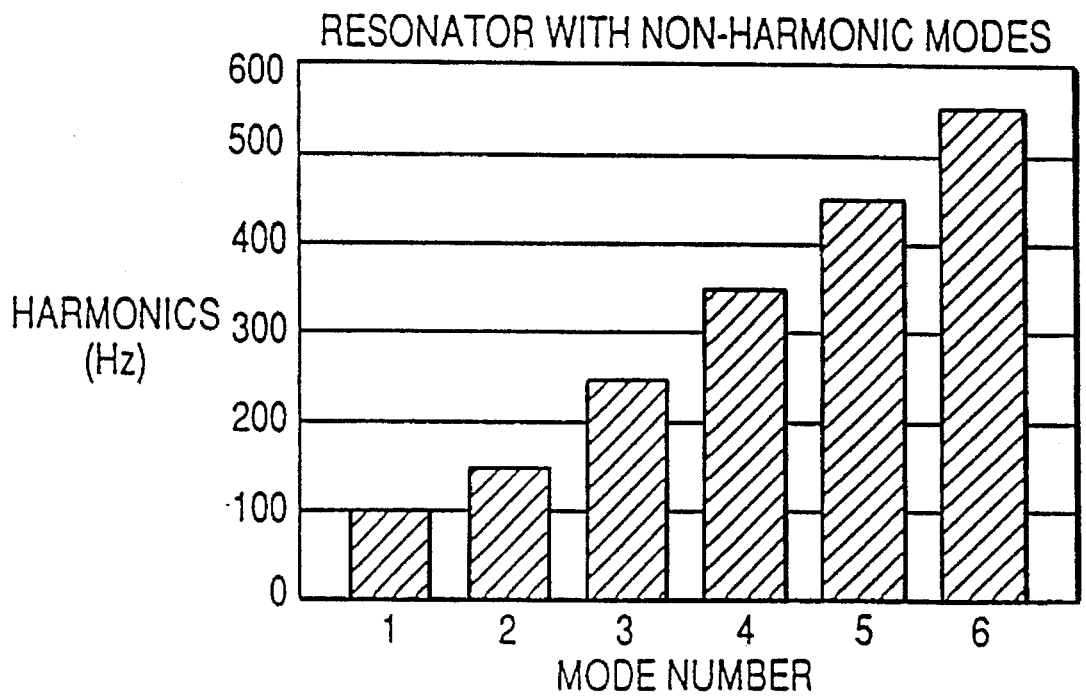
FIG. 2 is a graphical representation of a resonator having higher modes which are not harmonics of the fundamental.

The bar graph of FIG. 2 illustrates one of many possible arrangements for promoting the destructive self-interference of harmonics. In FIG. 2, the resonator modes are aligned to fall between the wave harmonics. For this example, the resonator modes have been shifted down in frequency so that the nth mode lies between harmonics n and n−1. With this arrangement a large degree of destructive self-interference of the wave harmonics can occur.

Figures 3, 4:
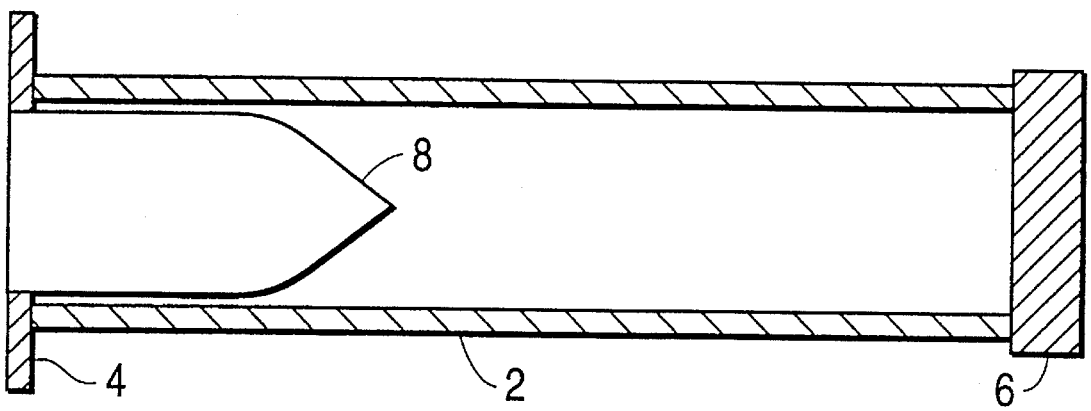
FIG. 3 is a sectional view of an embodiment of a resonator in accordance with the present invention, which employs an insert as a means of mode tuning.
FIG. 4 is a table of measured data for the resonator shown in FIG. 3.

FIG. 3 is a sectional view of a resonator which was constructed and tested, and whose modes are shifted down in frequency. The resonator in FIG. 3 is formed by a hollow cylindrical chamber 2, an end flange 4, an end flange 6, and tapered rod insert 8, with all parts being aluminum. Tapered rod insert 8 was welded to end flange 4 with end flange 4 being welded to chamber 2. End flange 6 was welded to chamber 2, and was drilled to accommodate a process tube and a pressure transducer. Chamber 2 has an inside diameter of 5.71 cm, and an inside length of 27 cm. Tapered rod insert 8 has a half-angle end taper of 34.98°, and a length of 10 cm, measured from end flange 4. Sharp edges on tapered rod insert 8 were rounded off to an arbitrary curvature to reduce turbulence.

Tapered rod insert 8 serves to create a smaller cross-sectional area along its length inside of chamber 2. In this way, the resonator of FIG. 3 is divided into two sections of different cross-sectional area, each section having its own acoustical impedance. This impedance change results in a shifting of the resonator modes to non-harmonic frequencies. The degree to which the modes are shifted can be controlled by varying the diameter and length of tapered rod insert 8. The manner in which the resonator is driven is described below.

FIG. 4 is a table of measured data obtained for the resonator of FIG. 3. The last column provides a relative measure of the degree of mode shift, by calculating the difference between the frequency "$f_n$" of the nth mode and n times the fundamental frequency "$nf_1$." The ideal mode shift, for placing the resonator modes at the midpoints between neighboring harmonics, is equal to ½ the fundamental frequency. For the FIG. 3 resonator, the ideal shift is $f_1/2=166.97$ Hz. For CCS resonators, the mode shift $f_n-nf_1=0$ for each mode by definition.

The resonator design of FIG. 3 does not provide ideal mode shifts, but comes close enough to provide significant results. This is due to the fact that the Fourier sum of the first few harmonics contributes heavily to shock formation. Thus, significant cancellation of the 2nd, 3rd, and 4th harmonics will reduce shock formation greatly. When the resonator of FIG. 3 was pressurized to 80 psia with gaseous refrigerant HFC-134a, 11.8 Watts of acoustic input power was required to achieve a 42 psia peak-to-peak pressure amplitude (measured at end flange 4). This is within 30% of the required driving power predicted by a strictly linear theory which accounts for only thermal and viscous boundary layer losses. At these operating conditions the amplitude of the 2nd harmonic was 20 dB down from the fundamental, with higher harmonics being down 30 dB or more.

Figures 5, 6:
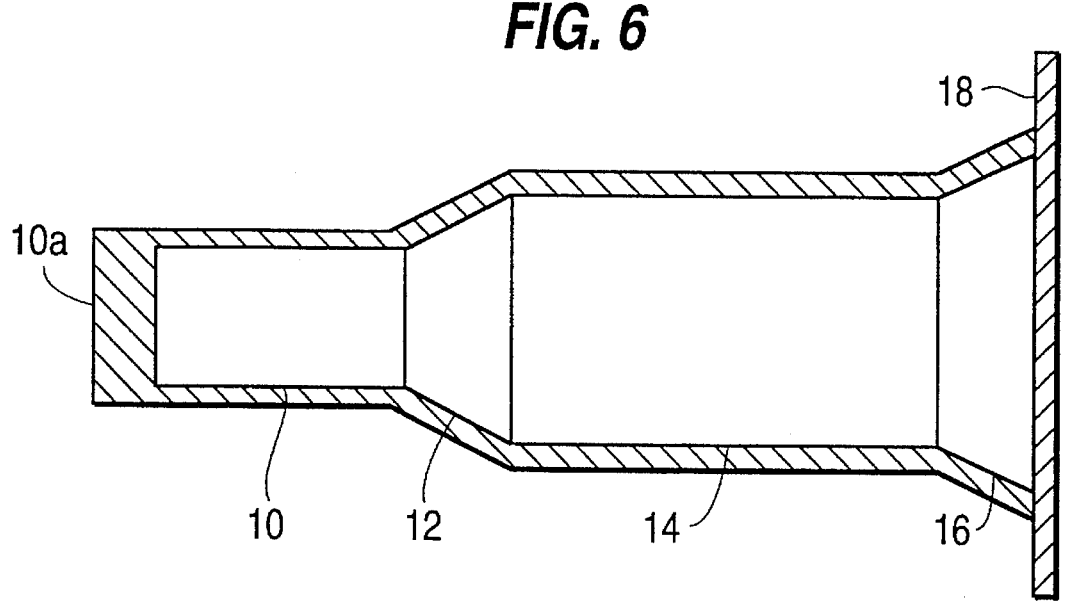
FIG. 5 is a table of theoretical data for the resonator shown in FIG. 3.
FIG. 6 is a sectional view of an embodiment of a resonator in accordance with the present invention which employs sections of different diameter as a means of mode tuning.

FIG. 5 is a table of theoretical data which was generated for the FIG. 3 resonator. Ideally, $f_n-nf_1$ should be approximately equal to the ideal shift for each of the resonator modes. However, it can be seen in FIG. 5 that the degree of mode shifting increases with mode number. At the 6th mode, shifting has increased so much that the mode frequency is now nearly coincident with the 5th harmonic of the wave. With more advanced resonator designs, many modes can be simultaneously tuned to lie between the wave harmonics. As the number of properly tuned modes increases, the resonator's linearity increases.

FIG. 6 is a sectional view of another resonator which was constructed and tested. The resonator in FIG. 6 has a chamber which is formed by a small diameter section 10, a conical section 12, a large diameter section 14, a conical taper 16, and an end flange 18. The chamber comprising the small diameter section 10, the conical section 12, the large diameter section 14, and the conical taper 16 were all machined from a single piece of aluminum. Aluminum end flange 18 was welded to conical end taper 16. Small diameter section 10 has a length of 7.28 cm and a diameter of 3.81 cm. Conical section 12 has a half-angle of 25.63° and an inside length of 3.72 cm. Large diameter section 14 has an inside length of 13.16 cm and an inside diameter of 7.38 cm. Conical taper 16 has a half-angle of 26.08° and an inside length of 2.84 cm. Section 10 and section 14 divide the resonator into two sections of different cross-sectional area, each section having its own acoustical impedance. This design results in a downward shifting of the resonator modes to non-harmonic frequencies.

The FIG. 6 resonator eliminates the tapered rod insert of FIG. 3, thereby reducing the internal surface area of the resonator, which in turn reduces the thermal and viscous boundary layer losses. The degree to which the modes are shifted can be controlled by varying the dimensions of section 10, section 14, conical section 12, and taper 16. Taper 16 compensates for excessive downward shifting of the higher modes, by shifting primarily the higher modes up in frequency. The manner in which the resonator is driven is described below.

FIG. 7 and FIG. 8 are tables of the measured data and theoretical data, respectively, for the resonator of FIG. 6. In comparison with the FIG. 3 resonator, the FIG. 6 resonator has improved the tuning of the 2nd, 3rd, and 4th modes, as well as reduced the excessive shifting of higher modes. The FIG. 6 resonator brings the 2nd, 3rd, and 4th modes much closer to the ideal shift, and results in improved performance.

When the resonator of FIG. 6 was pressurized to 80 psia, with gaseous refrigerant HFC-134a, pressure amplitudes of up to 100 psi peak-to-peak (measured at an end 10a of small diameter section 10) were achieved without shock formation. However, turbulence was evident, indicating that the acoustic velocity was high enough to cause non-laminar flow. As shown below, resonator geometry can be altered to greatly reduce acoustic velocity. At 60 psi peak-to-peak (measured at the end 10a of small diameter section 10) all harmonics were more than 25 dB down from the amplitude of the fundamental, for the FIG. 6 resonator.

In general, the modes of a given resonator geometry can be calculated from the general solution of the wave equation written for both pressure and velocity:

$$P(x)=A\cos(kx)+B\sin(kx)$$

$$V(x)=i/(\rho c)(A\cos(kx)+B\sin(kx))$$

where $i=(-1)^{1/2}$, $\rho$=average fluid density, c=speed of sound. The arbitrary complex constants A and B are found by applying the boundary conditions of the resonator to the above equations for P(x) and V(x). Resonators embodying the present invention were designed by iterating P(x) and V(x) in the frequency domain across finite elements of the resonator, until zero velocity is reached at the resonator's end. As demonstrated above, the mid-harmonic placement of resonator modes provides one of many ways to exploit the MACH principle. For more exact predictions of harmonic cancellation, the harmonics can be treated as waves traveling within the boundaries of the resonator, while accounting for their self-interference. The goal of which is to show harmonic self-cancellation as a function of changes in the resonator geometry.

Importance of the MACH Principle

It is revealing to compare the performance of MACH resonators with that of CCS resonators which do not restrict shock formation. As a comparison, consider the normal evolution to shock formation which occurs as a finite amplitude wave propagates. Using the method of Pierce, it is possible to calculate the distance a 60 psi peak-to-peak pressure wave must travel for a fully developed shock wave to evolve (Allan D. Pierce, *Acoustics*, p.571 (Acoustical Society of America 1989)). For a mean pressure of 80 psia (in gaseous HFC-134a), the waveform will evolve from a sinusoid to a shock after traveling only 22 cm, which is less than one traverse of the 27 cm length of the FIG. 6 resonator! From this it is easy to appreciate the longstanding assumption that at extremely high amplitudes, intrinsic nonlinearities of a gas will dominate any resonator design considerations.

Other Resonator Design Parameters

To efficiently create high amplitude resonant acoustic waves, it is important to keep the resonator boundary layer viscous and thermal losses as low as possible. Also, the acoustic velocity, associated with a desired pressure amplitude should be minimized to avoid excessive turbulence.

For a pure sinusoidal standing wave in a resonator of constant cross-sectional area, the peak acoustic velocity is equal to P/($\rho$c), where P≡peak acoustic pressure amplitude, $\rho$≡average fluid density, and c≡speed of sound at the average pressure. In practice, the peak acoustic velocity can be decreased by the proper resonator geometry. For example, the resonator of FIG. 6 has a peak acoustic velocity equal to 0.82(P/($\rho$c)) (P being measured at the end 10a of small diameter section 10), due to the expansion at the center of the chamber provided by conical section 12. This increase in cross-sectional area occurs just before the velocity maxima at the center of the chamber, thereby lowering the acoustic velocity.

Expansions, like those of the FIG. 6 resonator, have other advantages as well. When the acoustic velocity is reduced, boundary layer viscous losses are reduced. Also, the expansion reduces the peak acoustic pressure amplitude at end flange 18, thereby reducing boundary layer thermal losses at this end of the resonator. Similarly, the expansion provided by end taper 16 of FIG. 6 further reduces the boundary layer thermal losses. When the position of an expansion, like conical section 12 of FIG. 6, is varied along the length of the resonator, the boundary layer thermal losses and the boundary layer viscous losses will vary. It has been found theoretically that the sum of these losses reaches a minimum when the expansion is centered at approximately 0.3 of the length of the resonator.

Figure 9:
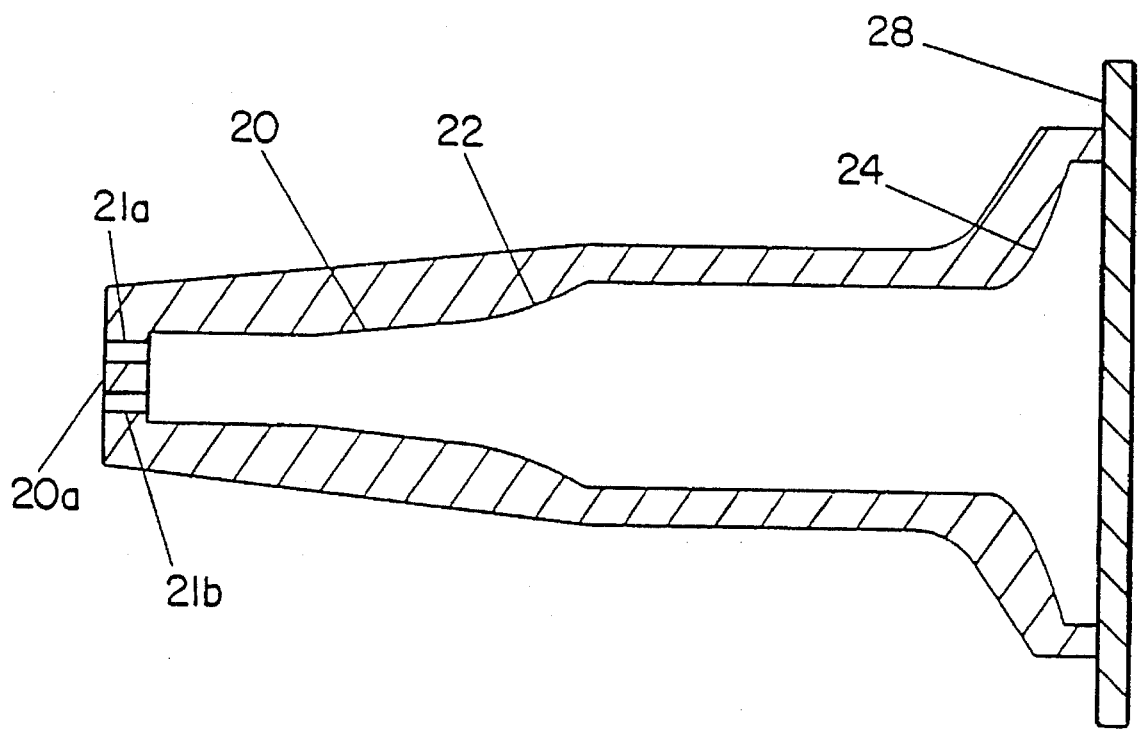
FIG. 9 is a sectional view of an embodiment of a resonator in accordance with the present invention showing further optimizations in resonator geometry.

In general, practical energy efficient resonator designs require a compromise between mode tuning for harmonic cancellation, minimizing acoustic velocity, and minimizing thermal and viscous losses. FIG. 9 is a sectional view of a resonator which represents one of a vast number of possible compromises between these design parameters.

The FIG. 9 resonator chamber has a conical expansion section 20, a curved expansion section 22, a curved end taper section 24, and an end flange 28. Ports 21a, 21b, such as an inlet and outlet or valves, are provided at an end 20a of the resonator. Although not shown, such ports are also provided in the resonators of FIGS. 3 and 6. The resonator chamber is preferably formed by a low thermal conductivity material such as fiberglass, since this will reduce the boundary layer thermal losses. However, any material, such as aluminum, which can be formed into a desired configuration can be used. The FIG. 9 resonator is similar in principle to the FIG. 6 resonator in its method of modal tuning, except for the curved sections which provide greater mode tuning selectivity. This selectivity is due to the varying rate of change of cross-sectional area provided by the curved sections, which is explained as follows. The magnitude of frequency shift of a mode, caused by a given area change, depends on which part of the standing wave pattern encounters the area change. Each of the many superimposed standing wave patterns in a resonator will encounter a fixed area change at a different point along its wave pattern. Thus, an area change which tunes one mode properly may cause unfavorable tuning for another mode. Curved sections can provide compensation for this unfavorable tuning by exposing different modes to different rates of area change. The term "curved section" is not intended to refer to a specific mathematical surface. Rather, the term "curved section" is understood to mean in general any section which provides a rate of change of area, as a function of the longitudinal dimension, whose derivative is non-zero. Any number of mathematical surfaces can be employed. It is contemplated that one possible set of equations for the curved expansion section 22 and curved end tapered section 24 could be as follows.

In FIG. 9 the constant diameter section at end 20a of the resonator has an inner diameter of 2.54 cm and is 4.86 cm long. Conical expansion section 20 is 4.1 cm long and has a 5.8° half-angle. Curved expansion section 22 is 3.68 cm long. To the right of curved section 22, the diameter remains constant at 5.77 cm over a distance of 11.34 cm. Curved end taper 24 is 2.16 cm long. To the right of curved end taper 24, the diameter remains constant at 13 cm over a distance of 0.86 cm. Curved expansion section 22 was described in a finite element program by the equation $D_n = D_{n-1} + 0.00003(7+n)$, and curved end taper 24 was described by the equation $D_n = D_{n-1} + 0.00038(n)$, where $D_n \equiv$ the diameter of the current element, and $D_{n-1} \equiv$ the diameter of the previous element, and with each element having a length 0.00108 meters.

FIG. 10 is a table of theoretical data for the FIG. 9 resonator, which shows that the point at which modes and harmonics overlap in frequency has been significantly extended to higher frequencies.

The FIG. 9 resonator also reduces the acoustic velocity to a value of $0.58(P/(\rho c))$ (P being measured at a small diameter end 20a of the resonator), which represents a significant reduction in acoustic velocity for the desired pressure amplitude. In addition, the FIG. 9 resonator reduces the total thermal and viscous energy dissipation of the FIG. 6 resonator by a factor of 1.50. Neglecting turbulent losses, the total rate of thermal and viscous energy loss, at a given pressure amplitude, is equal to the acoustic input power required to sustain that pressure amplitude. Thus, reducing thermal and viscous energy losses will increase energy efficiency.

Half-Peak Entire-Resonator Driving

The odd modes of a resonator can be effectively driven by mechanically oscillating the entire resonator along its longitudinal axis. This is the preferred method used by the resonators of the present invention. Although the resonators of FIG. 3, FIG. 6, and FIG. 9 could be driven by coupling a moving piston to an open-ended resonator, this approach has certain disadvantages which are avoided by the entire resonator driving method.

Entire resonator driving can be understood as follows. If the entire resonator is oscillated along its longitudinal axis, then the end caps will act as pistons. The odd mode pressure oscillations at the two opposite ends of a double-terminated resonator will be 180° out of phase with each other. Consequently, when the entire resonator is oscillated, its end caps, or terminations, can be used to drive an odd mode in the proper phase at each end of the resonator. In this way, the fundamental mode can be effectively driven.

Figure 11:
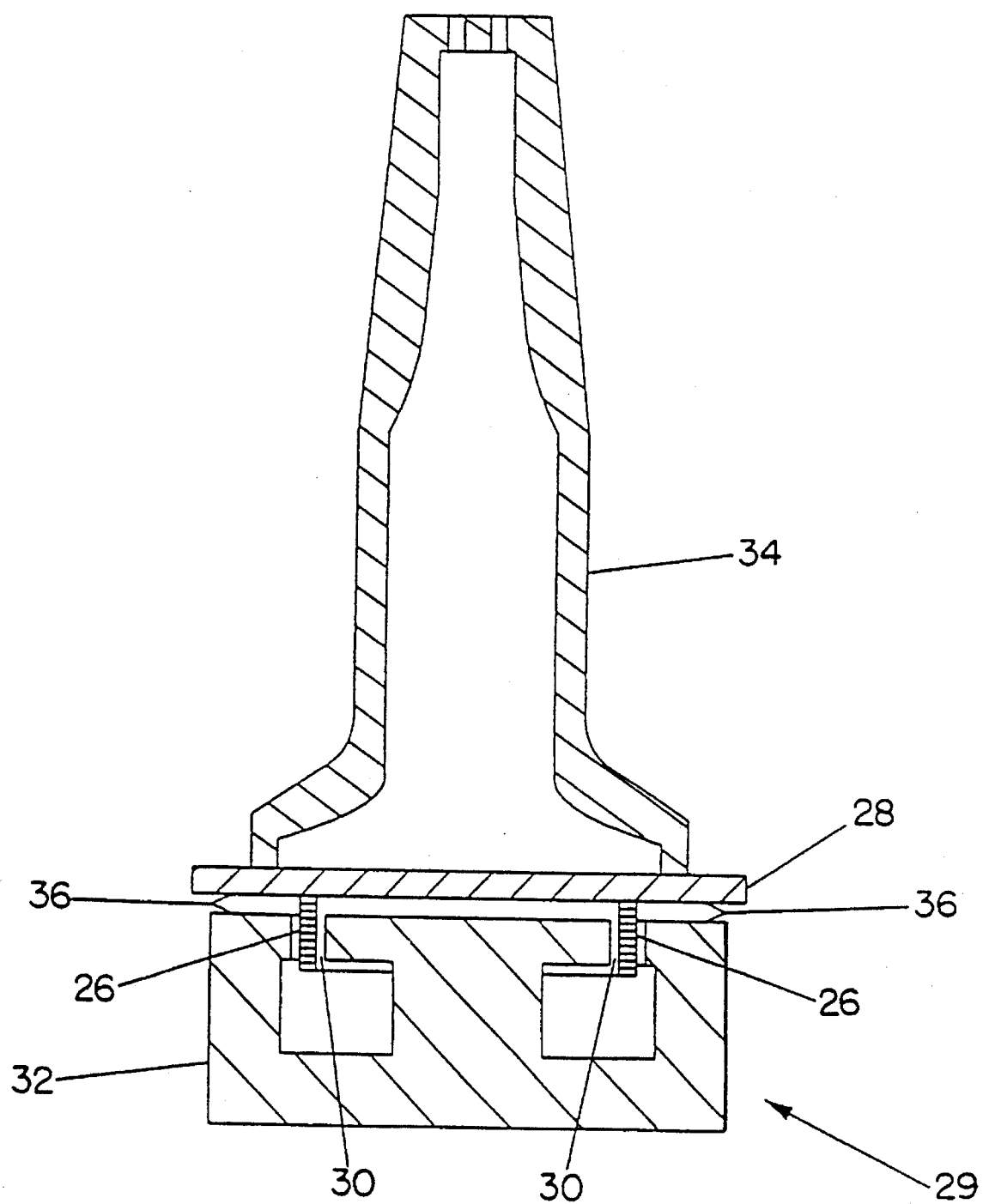
FIG. 11 is a sectional view of an apparatus used in a resonator driving system in accordance with the present invention, in which the entire resonator is oscillated along its longitudinal axis.

FIG. 11 is a sectional view of one of many approaches which can be used to drive an entire resonator. In FIG. 11 an electrodynamic shaker or driver 29 is provided, having a current conducting coil 26 rigidly attached to end flange 28 of resonator 34, and occupying air gap 30 of magnet 32. Magnet 32 is attached to end flange 28 by a flexible bellows 36. Bellows 36 maintains proper alignment of coil 26 within air gap 30.

When coil 26 is energized by an oscillating current, the resulting electromagnetic forces will cause resonator 34 to be mechanically oscillated along its longitudinal axis. Magnet 32 can be rigidly restrained so as to have infinite mass relative to resonator 34. In the preferred embodiment, magnet 32 is left unrestrained and thus free to move in opposition to resonator 34. In either case, an appropriate spring constant can be chosen for bellows 36 to produce a mechanical resonance equal to the acoustic resonance, resulting in higher electro-acoustic efficiency. Bellows 36 could be replaced by other components such as flexible diaphragms, magnetic springs, or more conventional springs made of appropriate materials.

Entire resonator driving reduces the mechanical displacement required to achieve a given pressure amplitude. When driving the entire resonator, both ends of the resonator act as pistons. In most cases, entire resonator driving requires roughly half the peak mechanical displacement which would be needed for a single coupled-piston arrangement.

Half-Peak Entire-Resonator (HPER) driving provides the following advantages. As discussed above, the proper tuning of modes of a chamber is critical to efficiently achieving high acoustic pressure amplitudes. It follows that this tuning must remain constant during operation. Resonators which are terminated on both ends will maintain precise tuning during operation and throughout the Lifetime of the resonator.

A further advantage relates to the use of HPER driving for acoustic compressors. Since HPER driven chambers are sealed, there are no oil-dependant moving parts that come in contact with the fluid being compressed; resulting in an inherently off-free compressor. The suction and discharge valves needed for acoustic compressors would typically be placed at the narrow end of a resonator, where the pressure amplitudes are the greatest. For example, valve placement for the resonator of FIG. 9 would be positioned at ports 21a, 21b at end 20a. The ratio of pressure amplitudes at the two ends of the FIG. 9 resonator is approximately 3:1 (left to right).

Non-Sinusoidal Driving

As discussed above, a properly designed MACH chamber will cause the higher harmonics of its fundamental to be self canceling. For the same reason, a MACH chamber will tend to cancel out harmonics which may be present in the driver's displacement waveform. Thus, MACH chambers can convert a non-sinusoidal driving displacement into a sinusoidal pressure oscillation. In addition, any mechanical resonance present in a driver, like the driver of FIG. 11, would tend to convert a non-sinusoidal driving current into a sinusoidal displacement waveform.

In some applications, the use of non-sinusoidal driving signals can result in greater overall efficiency. For example, the power amplifiers needed for driving linear motors can be designed to operate very efficiently in a pulsed output mode. Current pulses can be timed to occur once every acoustic cycle or to skip several acoustic cycles.

Another type of non-sinusoidal driving, which MACH chambers can facilitate, is a fluid's direct absorption of electromagnetic energy, as disclosed in U.S. Pat. No. 5,020,977, the entire content of which is hereby incorporated by reference. Pulsed microwave and infrared energy, when passed through an absorptive fluid, will create acoustic waves in the fluid. This electromagnetic-to-acoustic conversion will tend to result in very harmonic-rich acoustic waves. MACH chambers will tend to cancel the resulting harmonics, thereby promoting a sinusoidal pressure oscillation. Electromagnetic pulses can be timed to occur once per acoustic cycle, or to skip several acoustic cycles.

Porous Materials

Porous materials, such as sintered metals, ceramics, and wire mesh screens are commonly used in the field of noise control. Porous materials can provide acoustic transmission and refection coefficients which vary as a function of frequency and acoustic velocity. Properly placed within a resonator, these materials can be used as an aid to mode tuning.

Figure 12:
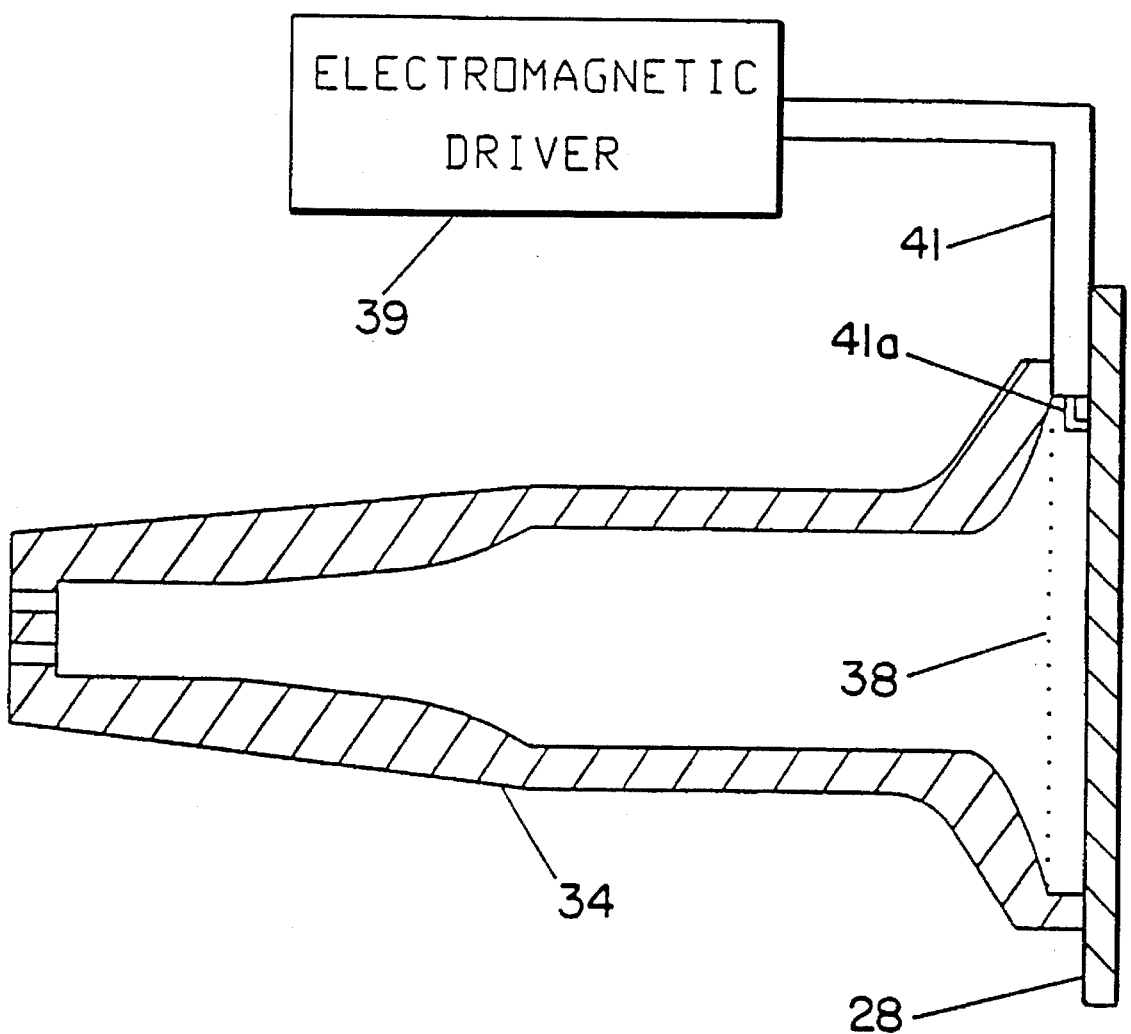
FIG. 12 is a sectional view of the resonator shown in FIG. 9 which employs porous materials for enhanced cancellation of higher harmonics.

FIG. 12 is a sectional view of a resonator 34 illustrating one of many possible uses of porous materials. In FIG. 12 a porous material 38 is rigidly mounted near end flange 28 of resonator 34. Porous material 38 will have a minimal effect on the fundamental of the resonator, whose acoustic velocity, becomes small near the surface of end flange 28. The higher modes of the resonator can have velocity maxima near the position of porous material 38. Thus, the higher harmonics of the wave can experience larger reflection coefficients at the porous material and be reflected so as to promote destructive self-interference. Tuning can be adjusted by varying the position of porous material 38 along the length of resonator 34.

In this way, a porous material can be used as an aid in optimizing the destructive self-interference of harmonics. The design flexibility provided by porous materials allows more aggressive optimization of specific resonator parameters, such as reducing the fundamental's acoustic velocity, without losing the desired mode tuning.

For microwave driven resonators, porous material 38 could also act together with end flange 28 to form a microwave cavity for the introduction of microwave energy into resonator 34. FIG. 12 illustrates an electromagnetic driver 39 coupled to the resonator 34 by a coaxial cable 41 having a loop termination 41a inside the resonator 34 in the area between the porous material 38 and end flange 28. The microwave energy would be restricted to the area between porous material 38 and end flange 28.

Figure 13:
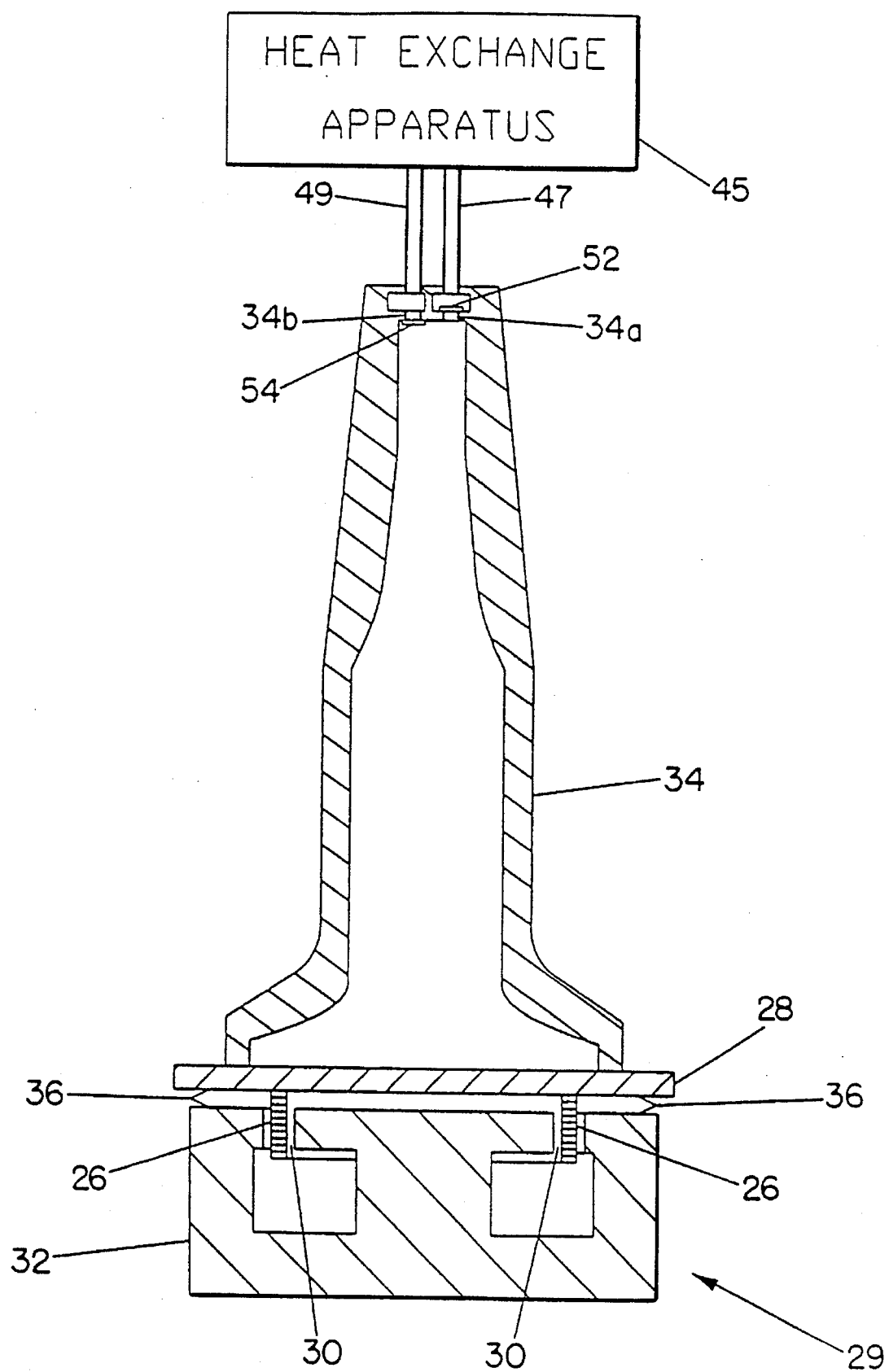
FIG. 13 is a sectional view of the resonator and driving system of FIG. 11 as connected to heat exchange apparatus to form a heat exchange system.

FIG. 13 is a sectional view of resonator 34 and drive apparatus 29 as used in a heat exchange system. In this case, ports 34a and 34b of resonator 34 are connected to a heat exchange apparatus 45 via conduits 47 and 49. Port 34a is provided with a discharge valve 52, and port 34b is provided with a suction valve 54. Discharge valve 52 and suction valve 54 will convert the oscillating pressure within resonator 34, into a net fluid flow through heat exchange apparatus 45. The heat exchange apparatus may include, for example, a conventional condenser and evaporator, so that the heat exchange system of FIG. 13 may form a vapor-compression system.

While the above description contains many specifications, these should not be construed as limitations on the scope of the invention, but rather as an exemplification of one preferred embodiment thereof. This preferred embodiment is based on my recognition that acoustic resonators can provide significant self-cancellation of harmonics, thereby providing extremely high amplitude acoustic waves without shock formation. The invention is also based on my recognition that other nonlinearities associated with finite amplitude waves, such as turbulence and boundary layer losses, can be reduced by proper resonator design.

Application of the MACH principle can provide nearly complete cancellation of wave harmonics. However, the present invention is not limited to resonators which provide complete cancellation. As shown in the above specifications, cancellation of a harmonic need not be complete to obtain shock-free high amplitude acoustic waves. Nor do all harmonics need to be canceled. There is a continuous range of partial harmonic cancellation which can be practiced. Harmonics can be present without shock formation, as long as their amplitudes are sufficiently small. Resonators which cancel one, two, or many harmonics could all be considered satisfactory, depending on the requirements of a particular application. Thus, the scope of the invention is not limited to any one specific resonator design.

There are many ways to exploit the basic features of the present invention which will readily occur to those skilled in the art. For example, shifting resonator modes to the midpoint between adjacent harmonics is only one of many ways to exploit the MACH principle. Resonator modes can be shifted to any degree as long as adequate self-destructive interference is provided for a given application.

In addition, many different resonator geometries can support standing waves and can be tuned to exploit the MACH principle. For example, a toroidal resonator can be tuned by using methods similar to the embodiments of the present invention. Although the present specification describes resonators whose modes are shifted down in frequency, similar resonator designs can shift modes up in frequency. For example, if the diameters of section 10 and section 14 in FIG. 6 are exchanged, then the resonator's modes will be shifted up in frequency rather than down. Furthermore, resonators can be designed to operate in resonant modes other than the fundamental, while still exploiting the MACH principle. Still further, the shock suppression provided by MACH resonators will occur for both liquids and gases.

Also, it is understood that the application of MACH resonators to acoustic compressors is not limited to vapor-compression heat transfer systems, but can be applied to any number of general applications where fluids must be compressed. For example, there are many industrial applications where oil-free compressors are required in order to prevent contamination of a fluid. Finally, many different drivers can be used with HPER driven resonators. For example, electromagnetic and piezoceramic drivers can also provide the forces required for entire resonator driving. In short, any driver that mechanically oscillates the entire resonator and provides the required forces can be used.

Accordingly, the scope of the invention should be determined not by the embodiments illustrated, but by the appended claims and their equivalents.

What is claimed is:

1. An electrodynamic driver for an acoustic resonator of a type having a chamber containing a fluid, said chamber having a geometry which produces destructive self-interference of at least one harmonic in said fluid to avoid shock wave formation at peak acoustic pressure amplitudes greater than 10% of mean pressure, said electrodynamic driver comprising:

a current conducting coil rigidly coupled to the acoustic resonator, said current conducting coil being periodically excited;

a magnet coupled to said current conducting coil; and a resilient device coupling said magnet to the acoustic resonator, a periodic excitation of said current conducting coil causing a periodic displacement of the acoustic resonator.

2. An electrodynamic driver as set forth in claim 1, wherein said resilient device comprises a spring having a spring constant which produces a mechanical resonance corresponding to a selected acoustic resonance of the acoustic resonator.

3. An electrodynamic driver as set forth in claim 1, wherein said magnet is free to move in opposition to the acoustic resonator.

4. An electrodynamic driver as set forth in claim 3, wherein said resilient device comprises a spring having a spring constant which produces a mechanical resonance corresponding to a selected acoustic resonance of the acoustic resonator.

5. An acoustic resonator driver having an acoustic resonator of a type having a chamber containing a fluid, said chamber having a geometry which produces destructive self-interference of at least one harmonic in said fluid to avoid shock wave formation at peak acoustic pressure amplitudes greater than 10% of mean pressure, said driver comprising:

a current conducting coil being rigidly attached to an acoustic resonator;

a magnet which receives the coil; and a spring attaching the magnet to the acoustic resonator;

wherein periodic excitation of the coil causes the resonator and magnet to move in periodic opposition to one another.

6. An acoustic resonator driver as set forth in claim 5, wherein the spring constant of the spring is chosen to provide a mechanical resonance, between the resonator and the magnet, whose frequency is equal to the driven acoustic resonance frequency of the resonator.

7. An acoustic resonator drive as set forth in claim 5, wherein the magnet is rigidly restrained, thereby preventing the magnet from moving in periodic opposition to the resonator.

8. An acoustic resonator driver as set forth in claim 5, wherein the magnet is unrestrained.

* * * * *